United States Patent [19]

Cocchi

[11] Patent Number: 4,863,427
[45] Date of Patent: Sep. 5, 1989

[54] SYRINGE FOR INJECTIONS, ESPECIALLY INTRAVENOUS MADE TO BE USED ONLY ONCE, WITHOUT ANY POSSIBILITY OF RE-ASPIRATION

[76] Inventor: Pietro Cocchi, Via Della Croce No. 27, Candeli, Fraz. Com. Bagno a Ripoli, Florence, Italy

[21] Appl. No.: 175,870

[22] Filed: Mar. 18, 1988

[30] Foreign Application Priority Data

Mar. 19, 1987 [IT] Italy ................... 9354 A/87

[51] Int. Cl.⁴ ............................................. A61M 5/00
[52] U.S. Cl. .................... 604/110; 604/218; 604/228
[58] Field of Search ............... 604/110, 111, 218, 187, 604/228

[56] References Cited

U.S. PATENT DOCUMENTS

| | | | |
|---|---|---|---|
| 3,941,129 | 3/1976 | Pleznac | 604/111 |
| 4,252,118 | 2/1981 | Richard et al. | 604/110 |
| 4,687,467 | 8/1987 | Cygielski | 604/110 |
| 4,699,614 | 10/1987 | Glazier | 604/228 X |
| 4,775,363 | 10/1988 | Sandsdalen | 604/228 X |

Primary Examiner—John D. Yasko
Attorney, Agent, or Firm—McGlew & Tuttle

[57] ABSTRACT

In a syringe for injections, especially intravenous —being realized so as to be used only once and comprising a body making up the cylinder to which the needle is fitted, a piston sliding in said cylinder and a piston handling member (stem) for recalling the piston during the liquid aspiration phase and for pushing the piston during the injection phase—said piston and said handling member (stem) are engaged with one another in a non-rigid way, in order to neutralize a further aspiration operation after a first phase of piston push has been carried out.

4 Claims, 4 Drawing Sheets

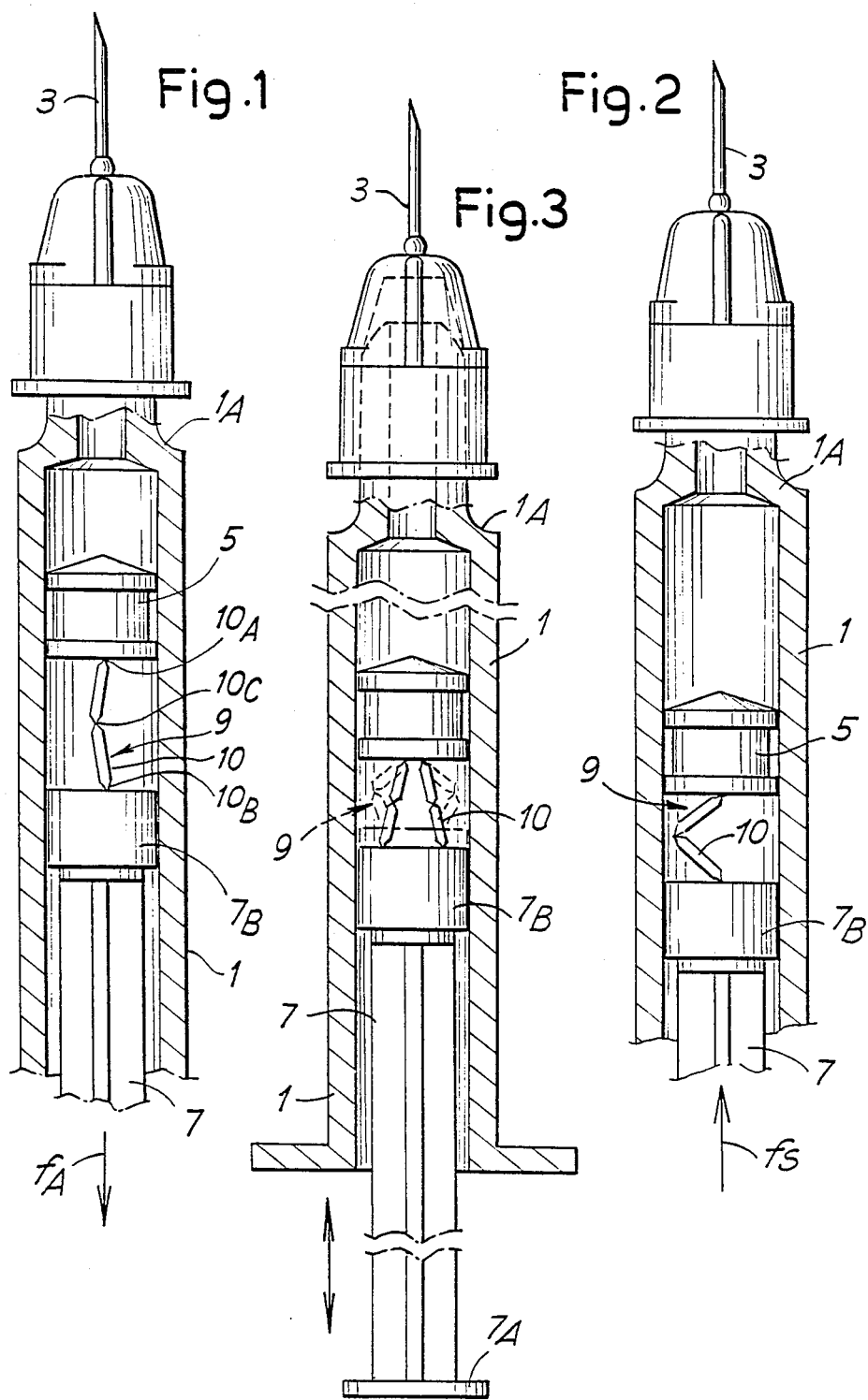

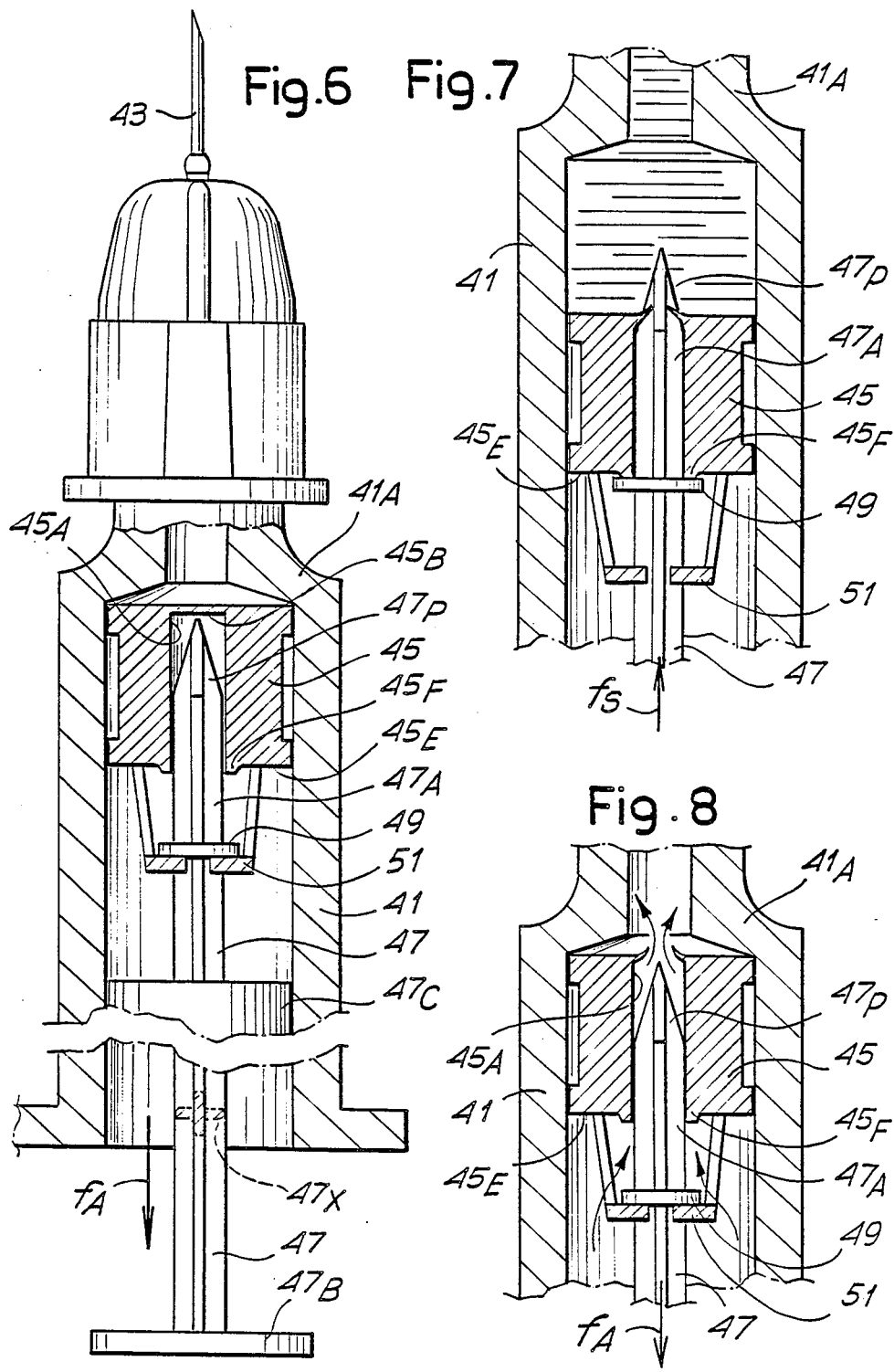

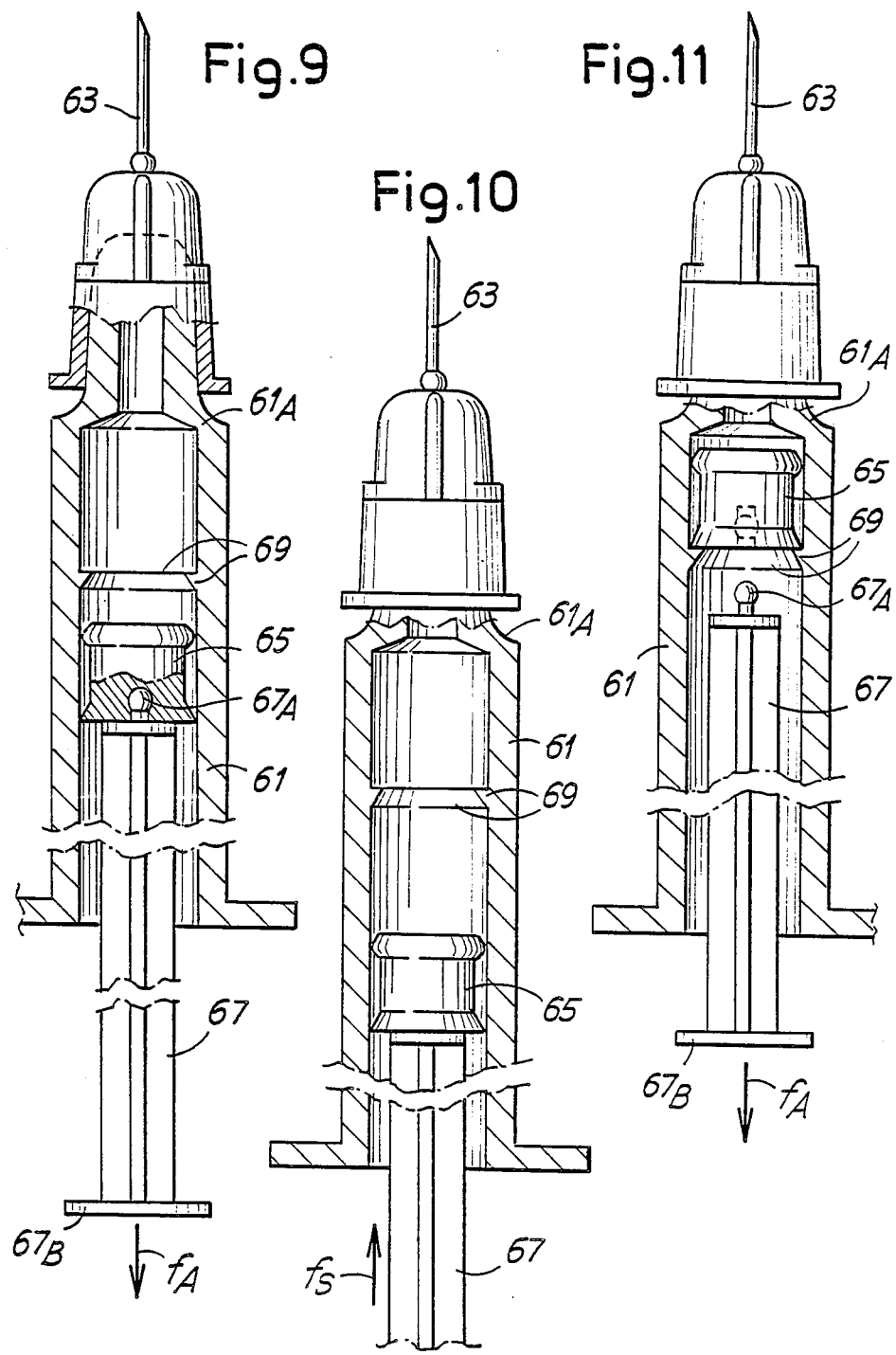

SYRINGE FOR INJECTIONS, ESPECIALLY INTRAVENOUS MADE TO BE USED ONLY ONCE, WITHOUT ANY POSSIBILITY OF RE-ASPIRATION

BACKGROUND OF THE INVENTION

1. Field of the Invention

The invention relates to syringes for intravenous and other injections, of the so-called "disposable" type, that is, to be used once.

It is well known that the sharing of syringes is the main cause for the spreading of hepatitis B and AIDS among drug addicts. The use of disposable syringes was expected to prevent the infections from spreading through such contagious channels owing to the specific purpose for which such syringes were devised and their low unit-cost. Unfortunately, this object has not been entirely achieved. The disposable syringes are actually used once only theoretically. It is in fact a common practice by drug addicts to use each disposable syringe more than once. Further the same syringe is often used by different drug addicts. This inevitably brings about the mutual exchange of small amounts of blood which are, however, sufficient to transmit infectious agents possibly present at haematic level, that is in the blood. In some cases, one syringe, one syringe may be used even by four or five different people, thereby multiplying enormously the possibility of infection and spread of these diseases.

p SUMMARY OF THE INVENTION

The object of the invention is to provide a syringe in which the possibility to be reused after a first injection is absolutely excluded, in order to limit the spread of infectious diseases like those above mentioned.

Substantially, a syringe for injections, especially intravenous, realized to be used only once and comprising a body making up the cylinder to which the needle is fitted, a piston sliding in said cylinder and a piston handling member (stem) for recalling the piston during the liquid aspiration phase and for pushing the piston during the injection phase, is characterized in that the piston and the handling member (stem) are engaged with one another in a non-rigid way, in order to neutralize a further aspiration operation after a first phase of piston push has been carried out.

In one embodiment the piston and the handling member (stem) are so connected as to remain in the relative mounting arrangement for the aspiration phase and take up a modified arrangement upon an attempt to carry out a further aspiration after a push exerted by the member (stem) onto the piston.

Practically, the handling member may be engaged with the piston through some limited axial clearance, and one of said members may have a perforation tip while the other has a lacerable wall; the disposition being such that the aspiration is carried out with the wall being integral, the push exerted for the injection causes the laceration of the all and the substantially hermetic seal in the piston, and a further aspiration operation causes an intake of air inside the syringe useful cavity defined by piston and cylinder, instead of a liquid aspiration. Advantageously, the peforating tip is carried by the handling member (stem), and the lacerable wall is formed by the piston.

In a modified embodiment, piston and handling member (stem) are engaged with one another through at least a link which resists tensile stress but fails, that is neutralizes itself, when compressed, thereby eliminating the transmission of a further pull action onto the piston after a push phase.

The link may be made up of at least an element which resists tensile stress and is broken by an axial compression action, the element being possibly realized in a single piece, that is integral with the piston and/or with the handling member.

The link may also be developed with two cooperating elements which are hooked up at the moment of preparation and during the pull-operated aspiration phase, while the push action causes a deterioration of, and the disengagement between, the elements to such an extent as to prevent a further pull action.

In a further embodiment, the handling member (stem) is engaged with the piston through a joint of limited tensile resistance, and between the piston and the cylinder an obstacle is provided against the sliding. This obstacle is to overcome for a further aspiration operation after the push phase, and is able to generate such a resistance as to disengage the handling member from the piston.

The obstacle may comprise an internal, - for example annular projection located inside the cylinder. This obstacle must be overcome, for the push phase, and this causes such a resistance against the sliding of the piston on a further aspiration phase as to give rise to the disengagement of the stem from the piston.

The joint may comprise a head that can be disengaged from its seat by exerting some effort, respectively by means of a tie rod having limited tensile resistance.

For the mounting of the piston, key means may be provided for going through an obturation body provided in the handling member (stem) and for acting on the piston.

The piston may also be shaped in such a way as to undergo a recall action by a vacuum produced in the variable volume chamber delimited by the cylinder and the piston. In order to effect the insertion of the piston into the cylinder, the cylinder may be formed with a suitable flare length. The vacuum can be advantageously generated through the pervious needle of the syringe.

The invention will be better understood by following the description and the attached drawings, which show a practical, non-limitative exemplification of the same invention. In the drawings, some feasible but nonlimitative embodiments of the invention are illustrated.

BRIEF DESCRIPTION OF THE DRAWINGS

FIGS. 1, 2, and 3 are a partial section and an elevational view of a syringe constructed in accordance with the invention from thereof embodiment and a modified form thereof;

FIGS. 6, 7 and 8 are similar views of a third embodiment; and

FIGS. 9, 10 and 11 are similar views of still another possible embodiment.

GENERAL DESCRIPTION OF THE DRAWINGS

Figure 4:
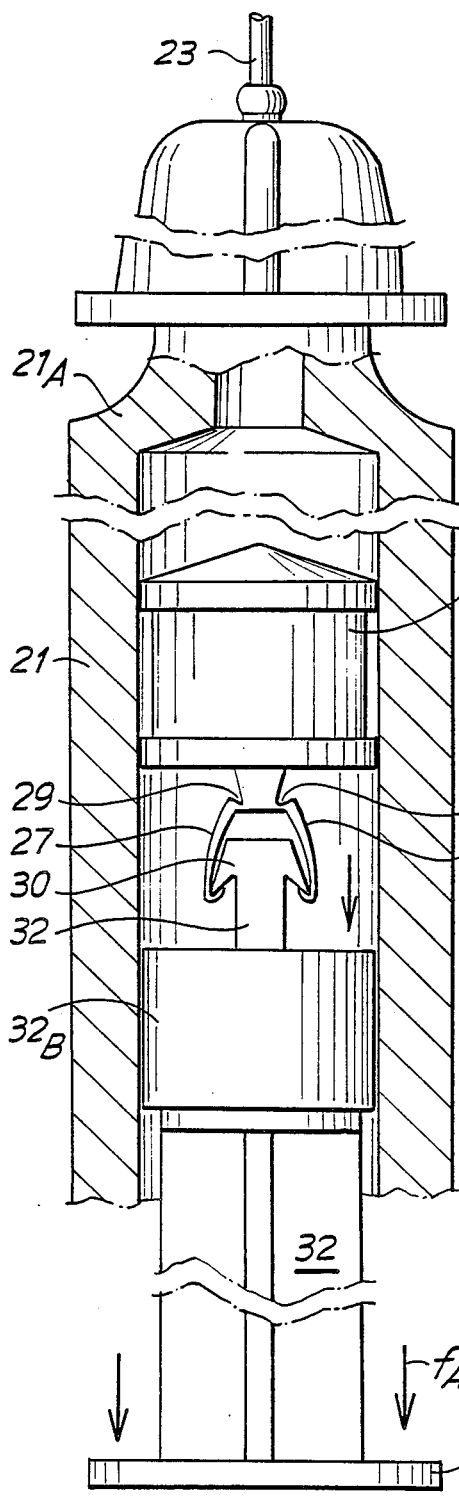
FIGS. 4 and 5 are similar views of a second embodiment.

According to what is illustrated in FIGS. 1, 2 and 3, numeral 1 indicates a syringe cylindrical body on which a needle 3 is fitted, or inserted. A piston 5 can slide in the cavity of the cylinder 1. The piston 5 must be moved away from the head 1A of the cylinder—where the needle 3 is inserted—in order to carry out the liquid aspiration through the pervious needle, and then moved again close to the head 1A to push the liquid through the needle into the tissues or into the vein.

To prevent a repetition of these two operating phases, according to the embodiment of FIGS. 1 to 3, the piston 5 is not driven directly by the stem 7 having the handling head 7A outside of the cylinder. Such drive is instead operated through a link 9 which resists tensile stress but fails under compression. In particular, the inner end of stem 7 has a guide expansion 7B, and a link 9 is provided between the piston 5 and the expansion 7B, in the form of at least a tie rod member 10 which resists tensile stress but breaks under compression owing to the force exerted by the assembly 7, 7A, 7B, in the direction of arrow fs in the push phase. This tie rod 10, which may be single (FIGS. 1 and 2) or double (FIG. 3), may be predisposed with breaking lines or points 10A and/or 10B and/or 10C, both at the junction with parts 7B and 5, and at an intermediate position. Owing to the characteristics of the material forming the tie rod 10 and/or the shape characteristics of the breaking zones 10A and 10B and/or 10C, and due also to a tie rod shaping that may favour the bending and thus the breaking upon the push according to arrow fs, it is possible to cause a recall effect of piston 5 according to arrow fA during the aspiration phase (FIG. 1). At the beginning of the push phase according to arrow fs, the tie rod 10 bends (according to a kneeling movement) and breaks at least on one of the above mentioned breaking points. Accordingly, the push is still exerted by the expansion 7B which acts directly on piston 5, but a new aspiration phase according to arrow fA is not possible because of the tie rod breaking that has taken place. The length size of the tie rod respectively of the cross-sections thereof defined by the breaking points will be such as to allow the bending and the breaking before the tie rod portions come to rest onto the inner wall of the cylinder.

Figure 5:
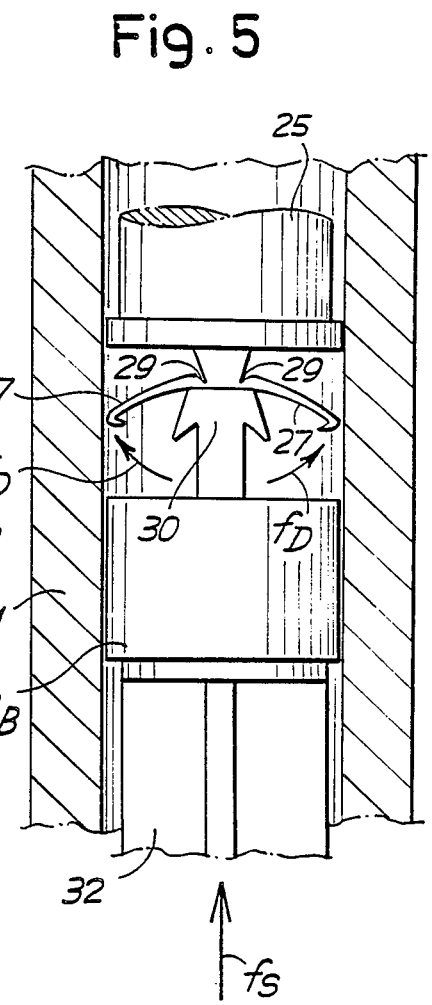

In the embodiment schematically illustrated in FIGS. 4 and 5, numeral 21 indicates the syringe cylindrical body on whose head 21A the needle 23 is inserted. Numeral 25 indicates the piston to be handled, which is characteristically formed with a pair of hooking appendixes 27, which extend from the external side of piston 25 opposite to the head 21A of the cylinder, and which are connected with the same piston through respective zones 29 of reduced cross-section. The zones 29 are capable of being easily deformed so as to determine a stretching apart, i.e. a straddle of the two hooking appendixes 27 according to arrow fD around the zones 29, due to a push action to be described herebelow. The hooking appendixes 27, which are so formed as to be close to one another, as shown in FIG. 4, engage, upon the syringe assembling a shaped head 30 of a stem 32 provided with a handling head 32A at the outer end of cylinder 21 and with a possible guide expansion 32B inside the same cylinder. The hooking head 30 is so shaped as to engage the hooking appendixes 27 when a pull action is exerted in the direction of arrow fA for the liquid aspiration through the pervious needle 23. At the beginning of the push phase for the injection according to arrow fs (FIG. 5), the head 30 moves close to piston 25 and by means of its own flattened end causes the deformation of the hooking appendixes 27 in the direction of their stretching apart or straddle movement according to arrows fD, around the zones 29 of reduced cross-section and of possible truncation. Accordingly, the hooking appendixes are stretched apart or even broken by piston 25, the stretching apart being permanent owing to the shaping and type of material used. It follows as a consequence that, if an attempt is made to repeat an aspiration phase according to arrow fA, the head 30 being no longer engaged with the appendixes 27 as shown in FIG. 5, the handling member 32, 32A, 30 and the piston 25, which should be recalled for the aspiration, are disengaged. It is thus impossible to carry out a second operation for the liquid aspiration.

The appendixes 27 may be in number of two, opposite and symmetrical and may have a laminar form, and the head 30 may have a prismatic form, and the disposition may have also a symmetry axis and be provided with a set of calyx-like appendixes 27 which stretch apart in the above mentioned way.

In the embodiment of FIGS. 6, 7 and 8, a cylinder 41 is provided, on whose head 41A the pervious needle 43 is inserted. Numeral 45 indicates the piston which is made to slide for the liquid aspiration and push operations.

According to this embodiment, the piston 45 exhibits a central seat 45A, which extends longitudinally and does not pass through but is obstructed, i.e. sealed by the presence of a membrane 45B which is easily lacerable but sufficient to permit the aspiration phase. The inner end 47A of a handling stem 47 is able to move in said seat 4A. This portion 47A of stem 47, or the whole stem, may have a star-like cross-section, as indicated by 47X. Stem 47 has, at the outer end, a handling head 47B. A guide expansion 47C may also be provided at an intermediate position of stem 47, able to cooperate with the inner wall of cylinder 41. Stem 47 has a shoulder 49 which separates the end portion 47A from the body of same stem. This shoulder 49 is disposed between the rear wall 45E of piston 45 and a bridge 51 which projects from the rear wall 45E of piston 45. Consequently the handling member made up of stem 47 with head 47B and end 47A is able to move with respect to piston 45 to an extent represented by the space in which the shoulder 49 can operate between the rear wall 45E of piston 45 and the bridge 51. The shoulder 49 forms also a valve head able to cooperate with a valve seat 45F provided in the rear wall 45E of the piston. The seat 45A is intended to guide the end portion 47A of stem 47 without any obstruction of same seat taking place, but instead, presenting a pervious section through said seat 45A, due to the shape of the cross-section—indicated by 47F—of said inner or end portion 47A of the stem. This portion 47A of the stem characteristically terminates with a tip 47P able to go through the membrane or diaphragm 45B and to lacerate it when the handling member 47b, 47, 49, 47A is pushed according to arrow fs.

By this arrangement, starting from the syringe assembling condition shown in FIG. 6, it is possible to recall the piston during the aspiration phase according to arrow fA, owing to the recall action of shoulder 49 on bridge 51 and thus on piston 45, the tip 47P being kept spaced apart from the membrane or diaphragm 45B. At the end of the aspiration phase and when the push phase begins according to arrow fs, the handling member moves forwards according to arrow fs with respect to piston 45 to an extent allowed to the shoulder 49 by the axial clearance between the bridge 51 and the wall 45E of the piston. Therefore, at the beginning of the push phase, the shoulder 49 moves to rest on the seat 45F formed in the rear wall 45E of piston 45, thus ensuring a sealing effect against the leak of liquid in a direction opposite to arrow fs, while tip 47P reaches and gets over the membrane or diaphragm 45B lacerating it, as shown in FIG. 7. Once the arrangement shown in FIG. 7 has been reached, the continuation of the push according to fs onto the assembly 47B, 47, 49, 47A causes the sliding of piston 45 and thus the defluxion of the liquid to be injected through needle 43. If, after this injection operation, that is, after the push phase, one wants to recall piston 45 again according to arrow fA for a new aspiration phase the arrangement of FIG. 8 and, afterwards, the piston displacement according to arrow fA could be obtained. Nevertheless, the result of this new aspiration phase would be a recall of air from the outside through the laceration of the membrane of diaphragm 45B and not an aspiration of liquid through the pervious needle 43. In fact, the liquid encounters a greater resistance in its flow through said needle (which is usually rather thin) then that encountered by the air penetrating into the volume-increasing cavity of the syringe through the slots of part 47A of stem 47 and through the seat 45A and the above mentioned lacerations. In this aspiration phase the shoulder 49 is moved away from the sealing seat 45F and made to lean on the bridge 51 in order to operate the recall of the piston according to fA.

Also in this case, therefore, there is a hindnrance in the re-utilization of the syringe.

FIGS. 9 to 11 show a further embodiment in which there is provided some resistance to the sliding of the piston for an aspiration phase following the completion of a push phase for the injection of previously recalled liquid.

In this embodiment, numeral 61 indicates the cylinder body on whose head 61A the needle 63 is inserted. Piston 65 is engaged with the handling stem 67 provided with external handling head 67B and possibly with an intermediate guide expansion, through a relatively little tensile-resistant link. In this example said link is shown in the form of a small expansion 67A of the inner end of stem 67, capable of engaging a seat formed by the piston 65, having a relatively limited undercut with respect to this head 67A. This arrangement may be achieved by utilizing a material, for the formation of piston 65 or the part thereof forming the seat for the head 67A, of sufficiently elastic or yielding characteristics.

In addition to this arrangement, a projection 69 is provided in the inner part of cylinder 61, that may be annularly continuous or circumscribed to small zones along the internal perimetrical development of the cylindrical cavity section of cylinder 61. These projections may be easily moulded through suitable dimensioning of projection 69, through the selection of the material employed for the cylindrical body 61 of the syringe and through suitable moulding techniques. The position of this internal projection 69 will be suitably chosen at a certain distance from head 61A of the syringe cylindrical body 61.

With this disposition, the assembly arrangement of the syringe shown in FIG. 9. allows the aspiration of liquid according to arrow fA, the piston 65 being on the opposite side of head 61A with respect to projection 69. Once the aspiration phase according to arrow fA has been carried out and, therefore, the condition of FIG. 10 has been achieved, the push phase is started according to arrow fs. To draw air out of the syringe, it is necessary, under these conditions, that piston 65 overcomes projection 69 which represents an obstacle to the sliding of same piston 65 but it is anyway of such a resistance, as to be overcome by the push on head 67A. Even when no care is taken in firstly drawing air out of the syringe, but the injection is simply made by directly inclining the needle downwards, the air cushion being present does not allow a sufficient pressure for the injection to be reached, however, it is necessary to reach and pass the projection 69 through piston 65, or at least through the front edge thereof. It should be noted that an injection operation in the presence of air can be relatively dangerous owing to the presence of the obstacle of projection 69 and the relatively high thrust that must be exerted on the piston in order to get over this obstacle and with the risk of injecting an air bubble into a vein. In any case, once piston 65, or at least the inner edge thereof, has passed the obstacle represented by projection 69, a new attempt to perform an aspiration according to arrow fA finds a relatively high resistance to the sliding of piston 65 which is retained by projection 69 thereby causing the disengagement of the handling member 67, 67A from piston 65. Consequently, piston 65 can no longer be moved from the position reached after the injection phase, as shown in FIG. 11, for operating a new aspiration phase according to arrow fA.

In any case the handling members will be so realized as to avoid piston handling makeshifts in order to obtain a second aspiration phase. Suitable expedients and mounting systems shall also be provided in order to maintain the integrity of the described members and thus their operatig capacity. In particular, in the case, for example, of the assembly of piston 5, suitable key passages shall have to be provided in the expansion 7B in order to act by means of a special tool on piston 5 for the insertion thereof into the cylinder without operating through an axial thrust onto stems 10. It will be practically impossible for the user to have at his disposal a corresponding key tool able to go through the expansion 7B and act on piston 5 for the push and thus injection phase without making use of the handling member 7, 7A, 7B. The insertion of piston 5 could also be provided through the effect of an abrupt suction, that is, by means of an abrupt vacuum to be created in the variable-volume cavity defined by cylinder 1 and piston 5 just presented in the cylinder in correspondence of a first flare length of the cylinder cavity provided for the piston initial insertion without any push, i.e. compression force, on stems 10. The assembly might be simply achieved by connecting the cylinder head 1A on the mouthpiece of a cylinder-piston group having a stated capacity that may be operated to generate an instantaneous abrupt vacuum degree in said variable-volume cavity.

Corresponding dispositions will be possibly provided for the solution of FIGS. 4 and 5, by always providing a diaphragm member, that is, an expansion 32B in the stem 32. Also in this case, any possibility of direct intervention by the user on piston 25 to operate a push must be avoided, and a mounting system of piston 25, which may also be carried out through a key tool or a vacuum effect, must be provided.

In the arrangement of FIGS. 6 and 8 a similar expedient may be provided for a key tool by which to get over the obstacle represented by expansion 47C or for a vacuum mounting arrangement as above described. In this solution of FIGS. 6 to 8 bridge 51 may also be realized in a suitable way in order to mount stem 47 with shoulder 49 inside the bridge. It may be provided, for example, that the bridge be made in two temporarily stretchable apart portions for the insertion of the shoulder, which may be relatively very limited width although still being able to realize a sealing on seat 45F. Also in this case a vacuum-operated mounting of piston 45 may be provided.

Specific monting expedients are not necessary in the case of FIGS. 9 to 11 when a link with a head 67A easily disengageable from piston 65 is realized. When, for such construction, it is desired to use a relatively weak tie rod—in order to perform the first aspiration therethrough without the resistance offered by the obstacle 69—but being subject to break when trying to perform a second aspiration from the position shown in FIG. 11 by overcoming the resistance offered by the obstacle 69, then it will be necessary to adopt an expedient similar to those above mentioned for the mounting of piston 65 as far as the position of FIG. 9.

The syringe according to the invention is automatically deactivated after the first use with a consequent impossibility of re-utilization. Said syringe is therefore useful in the fight against the spread of infectious diseases, in particular among drug addicts.

It is understood that the drawing shows an exemplification given only as a practical demonstration of the invention, as this may vary in the forms and dispositions without nevertheless departing from the scope of the idea on which the same invention is based.

I claim:

1. A syringe for injections, especially intravenous injections, to be used only once, comprising a cylinder, a needle inserted into said cylinder, a piston slidable in said cylinder and a piston handle member for recalling said piston during a liquid aspiration phase and for pushing the piston during an injection phase, joint means for providing a connection between said piston and said handle member, said joint means connection between said piston and said handle member being neutralized upon commencement of said injection phase before a second aspiration operation, in order to prevent a further aspiration operation, said handle member being joined to said piston with some limited axial clearance, and wherein one of said handle member and said piston has a perforating tip and the other of said handle members and said piston has a lacerable wall; the aspiration is carried out with said wall being integral, the thrust exerted for the injection causing the laceration of said lacerable wall preventing a further aspiration operation.

2. A syringe according to claim 1, wherein said perforating tip is carried by said handle member and said lacerable wall is formed by said piston.

3. A syringe comprising:
   a cylinder with a first end and a second end;
   a needle closing and extending out of said first end;
   a piston in said cylinder and in sliding engagement with said cylinder, said piston having a recess extending axially through said piston with a first end arranged toward said needle and an opposite orifice end, a membrane covering said piston first end, said piston orifice end having an annular seat, a recess length defined by the distance between said membrane and said annular seat;
   a stem having a handle portion extending out of said cylinder second end and arranged to fit slidably in said cylinder, said stem having a pointed arranged to fit in said recess, a shoulder on said stem between said handle portion and said pointed end and arranged to fit sealingly over said annular seal, a stem working distance defined by the distance between said shoulder and said pointed end, said working distance being substantially longer than said recess distance;
   a detent means connected to said piston, said stem being fitted through said detent means, said shoulder being movable between said piston annular seat and said detent means;
   said piston being pullable away from said needle by pulling said stem away from said needle effecting said shoulder to pull said detent means and said piston;
   said piston being pushable toward said needle by pushing said stem toward said needle effecting said shoulder to push said piston toward said needle and causing said pointed end to puncture said membrane.

4. A syringe, comprising a cylinder having a discharge end, and a discharge needle closing and extending out of said cylinder, a stem member having a handle portion extending outside of said cylinder on the end thereof opposite to said needle and having an inner portion with an expansion in slidable engagement with said cylinder, a floating piston in slidable engagement with said cylinder between said expansion and said needle, and discontinuing means defined between said expansion and said discontinuing means for allowing a first movement of said piston in a direction away from said needle to draw a liquid through said needle into said cylinder, and said discontinuing means for destroying the structural integrity of said syringe upon movement of said piston towards said needle to discharge the liquid through said needle thereafter discontinuing the effective pumping movement of said piston, said discontinuing means comprising a recess in said piston having a forward end closed by a membrane of said piston with said stem having a pointed end engageable with said membrane upon the first movement of said stem toward said needle to puncture said membrane to allow fluid to flow through said piston discontinuing its effective pumping movement upon a second movement upon said stem.

* * * * *